United States Patent [19]

Meierhoefer

[11] 4,104,214

[45] Aug. 1, 1978

[54] FLUID ABSORBENT CELLULOSE FIBERS CONTAINING ALKALINE SALTS OF POLYMERS OF ACRYLIC ACID, METHACRYLIC ACID OR AN ACRYLOAMIDOALKANE SULFONIC ACID WITH ALIPHATIC ESTERS OF ACRYLIC ACID OR METHACRYLIC ACID

[75] Inventor: Alan W. Meierhoefer, Gaithersburg, Md.

[73] Assignee: Akzona Incorporated, Asheville, N.C.

[21] Appl. No.: 746,539

[22] Filed: Dec. 1, 1976

[51] Int. Cl.² ............................................. C08L 1/02
[52] U.S. Cl. ..................... 260/17.4 CL; 128/285; 128/290 R; 128/296; 264/188; 264/194; 260/17.4 GC
[58] Field of Search ............... 260/17.4 GL; 128/284, 128/285, 290

[56] References Cited

U.S. PATENT DOCUMENTS

| 2,610,953 | 9/1952 | Daul et al. | 260/17.4 |
| 3,256,372 | 6/1966 | Adams | 260/17.4 |
| 3,445,556 | 5/1969 | Kuzmak | 260/17.4 |
| 3,457,198 | 7/1969 | Sobolev | 260/17.4 |
| 3,514,385 | 5/1970 | Magat et al. | 260/17.4 |
| 3,816,357 | 6/1974 | Church | 260/17.4 |
| 3,889,678 | 6/1975 | Chatterjee | 260/17.4 |
| 3,889,678 | 6/1975 | Chatterjee | 128/284 |
| 3,980,663 | 9/1976 | Gross | 526/14 |
| 3,995,998 | 12/1976 | Rowland et al. | 260/17.4 |
| 4,017,653 | 4/1977 | Gross | 128/285 |

*Primary Examiner*—Edward M. Woodberry
*Attorney, Agent, or Firm*—Francis W. Young; Jack H. Hall

[57] ABSTRACT

An alloyed cellulosic fiber containing an alkali metal salt or ammonium salt of a copolymer or terpolymer of acrylic acid and/or methacrylic acid and an aliphatic ester of at least one of the acids is prepared by a process wherein the copolymer or terpolymer is mixed with a viscose solution and the mixture is extruded through a spinneret into a conventional spin bath and processed into staple fibers which are adapted to be used in absorbent articles and the like. The alloyed cellulosic fiber of the invention has increased fluid absorbency characteristics over the fibers of the same cellulose composition without the alloying material. An unsaturated aliphatic dicarboxylic acid such as maleic acid or anhydride may be incorporated in the copolymer or terpolymer. Also, a copolymer or terpolymer of acrylic acid or methacrylic acid and an aliphatic ester of acrylic acid or methacrylic acid may contain radicals obtained from acryloamidoalkane sulfonic acid or an unsaturated phosphorous acid.

15 Claims, No Drawings

FLUID ABSORBENT CELLULOSE FIBERS CONTAINING ALKALINE SALTS OF POLYMERS OF ACRYLIC ACID, METHACRYLIC ACID OR AN ACRYLOAMIDOALKANE SULFONIC ACID WITH ALIPHATIC ESTERS OF ACRYLIC ACID OR METHACRYLIC ACID

This invention relates generally to cellulosic fibers and, more particularly, to a regenerated cellulose fiber having improved water and body fluid absorbency and to a process for preparing the fiber.

In accordance with the conventional viscose process, chemical cellulose from wood pulp or cotton linters is converted into regenerated cellulose by a series of steps in which the cellulose is first treated with a sodium hydroxide solution to mercerize it and to form alkali cellulose. The alkali cellulose, after aging, is reacted with carbon disulfide to form a soluble sodium xanthate derivative. The xanthated cellulose is later dissolved in dilute aqueous sodium hydroxide to form viscose which, after ripening, is spun by extrusion through a spinneret into a spin bath containing sulfuric acid and an alkali metal salt or an alkaline earth metal salt which coagulates the strands of viscose solution into individual filaments of regenerated cellulose. These filaments may be collected as a cake of a mass of filaments, processed into a tow and cut into staple fibers.

Staple fibers prepared by the viscose process are used extensively in making articles which are used to absorb water and body fluids such as, for example, surgical bandages, diapers, sanitary napkins, tampons and the like.

It has been proposed before to improve the absorbency of staple fibers of regenerated cellulose by alloying the regenerated cellulose with another material. For example, in accordance with the disclosure in U.S. Pat. No. 3,844,287, an alkali metal salt or ammonium salt of polyacrylic acid is mixed with the viscose solution before the solution is extruded to improve the absorbency characteristics of the fiber. In accordance with the disclosed process, a caustic solution of polyacrylic acid is mixed with viscose, the mixture is spun into a conventional coagulating bath and the resulting fiber is dried with an alkaline lubricating finish thereon. Such staple alloy fibers are known to be more absorbent and to have improved fluid retention properties over the nonalloyed regenerated cellulose fibers. However, the absorbency of such alloy fibers is not sufficient for the fibers to be entirely satisfactory for use in some absorbent articles.

It is an object of this invention to provide a process for making an alloy cellulosic fiber which has improved fluid absorbency and improved fluid retention. Another object of the invention is to provide a process for making an alloy fiber of regenerated cellulose containing a copolymer, terpolymer or the like which can be used to advantage in making articles for fluid absorbent applications. Still another object of the invention is to provide an article of manufacture containing a fiber of regenerated cellulose having improved absorbency for water and body fluids. A still further object of the invention is to improve the absorbency of regenerated cellulose fibers and the like for water and body fluids and to provide articles containing the fibers to be used in association with parts of the human body.

The foregoing objects and others are accomplished in accordance with this invention, generally speaking, by providing a process for making cellulosic fibers such as viscose rayon, hydroxypropyl cellulose and hydroxyethyl cellulose wherein an alkali metal salt or ammonium salt of a polymer of an aliphatic ester of acrylic acid or methacrylic acid and acrylic acid, methacrylic acid or an unsaturated sulfonic acid is incorporated in the fiber. In the viscose process for making rayon, the polymer is mixed with a viscose solution and the solution is spun to form an alloy regenerated cellulose fiber. The polymer may be (1) a copolymer of acrylic acid or methacrylic acid and an aliphatic ester of acrylic acid or methacrylic acid, (2) a terpolymer of acrylic acid, methacrylic acid and an aliphatic ester of acrylic acid or methacrylic acid, (3) a copolymer or terpolymer of acrylic acid, methacrylic acid, an aliphatic ester of acrylic acid and/or methacrylic acid and an unsaturated aliphatic dicarboxylic acid such as maleic acid or anhydride, (4) a copolymer or terpolymer of acrylic acid, methacrylic acid, an aliphatic ester of acrylic acid and/or methacrylic acid and an unsaturated sulfonic acid such as an acryloamidoalkane sulfonic acid or (5) a copolymer or terpolymer of acrylic acid, methacrylic acid, an aliphatic ester of acrylic acid and/or methacrylic acid and an unsaturated phosphorous acid such as vinyl phosphonic acid, (6) a copolymer of an unsaturated sulfonic acid and an aliphatic ester of acrylic acid or methacrylic acid, or various combinations of (1), (2), (3), (4), (5) and (6). The term "polymer" is used herein for the sake of convenience to include the copolymers abd terpolymers (1) through (6) and is not intended to include a homopolymer of acrylic acid or methacrylic acid. The polymer is mixed substantially uniformly with a spinnable viscose solution, the mixture is spun into a conventional spinning bath and the resulting regenerated cellulose fiber is processed into a staple fiber which is adapted to be used in an article to be used for absorbing water or body fluids. It has been found in accordance with this invention that the fluid absorbency and fluid retention of an alloy fiber of the type described are significantly greater than the fluid absorbency and fluid retention of fibers made from the same viscose solution without the addition of the alloying polymer. Although the invention contemplates broadly any alloyed cellulosic fiber containing any alkali metal or ammonium salt of the polymers which can be stretched, dried and otherwise processed into a product useful for making articles to be used for the absorption of body fluids, regenerated cellulose fibers containing the alkali metal salts of the copolymers of acrylic acid or methacrylic and an alkyl ester of acrylic acid or methacrylic acid are preferred.

In practicing the invention, a suitable viscose solution containing the polymer described above, cellulose, sodium hydroxide and carbon disulfide is prepared and extruded into a conventional spin bath such as one containing sulfuric acid, sodium sulfate and/or zinc sulfate or magnesium sulfate of predetermined concentrations, rinsed with water, stretched in air, finished, and dried as in conventional prior art processess. The viscose solution may be prepared first by conventional steps. This may include steeping conventional chemical cellulose sheet prepared from wood pulp or cotton linters in a caustic soda solution (NaOH) and thereafter removing caustic soda by pressing or the like to the desired solids content. The resulting alkali cellulose is shredded and, after aging, is mixed with carbon disulfide to form an aqueous alkaline xanthate (viscose) solution. For best results, the concentration of the viscose solution is from about 5 to 10 percent by weight cellulose, from about 4 to 8 percent by weight sodium hydroxide, from about 1.7 to 2.5 percent sulfur and the remainder water.

The alkali metal salt or ammonium salt of the polymer of the invention may be mixed with the viscose solution at any stage prior to spinning, preferably in an amount of from about 1 to about 20 percent by weight polymer based on the weight of cellulose in the solution. The polymer may be neutralized or partially neutralized with agueous ammonia or an alkali metal hydroxide such as sodium hydroxide, potassium hydroxide or lithium hydroxide. Preferably the polymer is neutralized or partially neutralized before it is added to the viscous solution. The neutralized or partially neutralized polymer is preferably mixed with the viscose by injection into the viscose solution just before the viscose solution is extruded. Alternately, the polymer may be added to the viscose solution without neutralization and sufficient alkali metal hydroxide or aqueous ammonium may be added to neutralize the polymer after it is mixed with the viscose solution.

In a preferred embodiment of the invention, the viscose solution containing the polymer of the invention is spun or extruded through spinneret openings into an acid bath where the cellulose fiber is regenerated. The regenerated fiber is stretched in air from 0 - 100%, or even higher, if desired, preferably from about 30% to 50% and then run through a hot aqueous bath maintained at a temperature of from ambient (20° C) to 100° C., preferably from 90°- 97° C. The hot aqueous bath may contain any amount of dilute sulfuric acid, magnesium sulfate, zinc sulfate, and sodium sulfate, and the like depending upon the characteristics desired in the fiber. The fiber may be subjected to a second stretching of from 0 to 100% in the hot bath. The total stretch in both steps is preferably within the range of 50% to 70%. The stretching, as is well known, imparts the necessary strength to the finished fiber. The fibers in the form of a large bundle of continuous filaments or tow from the combined output of a number of spinnerets are cut into short fibers of any desired length and dried to a moisture content of around 11% and baled.

After the fiber is regenerated in the acid bath, the alloying material occluded in the fiber may be in acid form. It must be at least partially in the form of the alkali metal or ammonium salt in order to achieve the highest degree of absorbency. It may be converted into the salt form during the alkaline sodium sulfide wash of the fiber which is conventionally used to remove metal and sulfur impurities. In some instances, it may be desirable, particularly, if an acid wash follows the sulfide, to treat the fiber with a base such as a dilute solution of sodium bicarbonate, sodium hydroxide, or the like, to complete the conversion to insure that a high percentage of the alloying polymer of the invention is in the salt form. It may be desirable to limit the amount of alloying polymer converted to the salt form for certain applications where the material may come into contact with the body, since a pH which is much higher than 7 to 7.5 can cause irritation of delicate membranes and serve to promote the growth of harmful microorganisms. Subsequently, a conventional finish, such as surfactant, may be applied and the staple fibers may be dried in a suitable hot air drier to a predetermined moisture content suited to the particular end use of the fiber. Preferably, the pH of the finished alloy fiber should be from about 5 to 7.5.

The copolymers of acrylic acid or methacrylic acid and an ester of acrylic acid or methacrylic acid may be prepared by any process known to be suitable for polymerizing or copolymerizing the acids. For example, a mixture of the acid or acids and ester may be heated in the presence of a suitable catalyst such as potassium persulfate or the like. A conventional chain transfer agent may be added to control the molecular weight. The copolymer may contain the acid and ester groupings in any suitable proportions such as for example, from 50% to 90% of acrylic acid or methacrylic acid and 50% to 10% by weight of the aliphatic ester of acrylic acid and/or methacrylic acid.

The aliphatic ester of acrylic acid and/or methacrylic acid may be prepared by reacting the acid with any suitable alcohol such as for example, methyl alcohol, ethyl alcohol, propyl alcohol, isopropyl alcohol, n-butyl alcohol, tertiary butyl alcohol, 2-ethyl hexyl alcohol, stearyl alcohol, or the like. Preferably, the aliphatic chain of the ester group derived from the alcohol will have 1 to 18 carbon atoms.

The alloying polymer of the invention may also contain groupings in the chain derived from an unsaturated aliphatic dicarboxylic acid such as, for example, maleic acid, fumaric acid, maleic anhydride, the mono-methyl or mono-propyl esters of maleic acid and the mono-methyl, mono-ethyl or mono-propyl esters of fumaric acid and the like. These polymers may be prepared by a process like that used for making a copolymer (1) or terpolymer (2) above with the exception that the aliphatic unsaturated dicarboxylic acid is mixed with the acrylic or methacrylic acid and ester.

The polymer of acrylic acid and/or methacrylic acid, an aliphatic ester of acrylic acid or methacrylic acid and sulfonic acid or unsaturated phosphonic acid may be prepared by mixing the monomers and sulfur or phosphorous compounds together and heating the mixture with a suitable catalyst. An acryloamidoalkane sulfonic acid or salt may be used to include the —$SO_3H$ grouping in the polymer. Suitable acryloamidoalkane sulfonic acids and salts for making a polymer with acrylic acid and/or methacrylic acid and an aliphatic ester are disclosed in U.S. Pat. No. 3,506,707 granted Apr. 14, 1970, the disclosure of which is incorporated herein by reference. The acryloamidoalkane sulfonic acids may also be reacted with the aliphatic ester of acrylic acid and/or methacrylic ester to form a suitable polymer without acrylic acid or methacrylic acid. The nitrile compound reacted with the intermediate formed by reaction of an olefinic compound with an aryl sulfate preferably has an alkyl group of 1 to 10 carbon atoms. An unsaturated phosphorous acid such as vinyl phosphonic acid may be used instead of the sulfonic acid or in combination therewith.

The present water retention as indicated by the secondary swelling of a rayon fiber may be determined by soaking 2 to 3 grams of previously washed and dried rayon fiber in water, and removing excess water by centrifuging at a force of 2500 to 3500 times gravity for 15 minutes in stainless steel sample holders. These holders are 22 mm. I.D. $\times$ 25 mm. deep, with screw caps to cover both ends. Space is provided in the centrifuge cup below the sample holder to contain the excess water which is removed from the yarn during centrifuging. The extracted fiber is placed in a preweighed weighing bottle; the weight of the swollen fiber is obtained and, after drying overnight at 105° C., the weight of the dry fiber is determined. The percent swelling is then determined by use of the following equation:

TABLE I

| Example No. | Polymer | WRV% | SRV% |
|---|---|---|---|
| I | none | 71 | 67 |
| II | acrylic acid | 112 | 95 |
| III | 90-10 AA/nBA* | 128 | 110 |
| IV | 80-20 AA/EA** | 116 | 111 |
| V | 90-10 AA/LMA*** | 143 | 118 |
| VI | 90-10 AMPS/nBA | 125 | 111 |

*acrylic acid - n-butyl acrylate
**acrylic acid - ethyl acrylate
***acrylic acid - lauryl methacrylate It can be seen from the results in Table I that the alloy regenerated cellulose fibers provided by this invention have improved water and body fluid absorbency over fibers prepared from the same viscose solution which does not contain the alloying polymer of the invention and over fibers containing a homopolymer of acrylic acid. Because of the improved absorbency characteristics of the fibers of the invention, they can be cut to staple fiber lengths and used to advantage in the manufacture of articles to be used for absorbing water and body fluids such as for example, surgical bandages, diapers, tampons, sanitary napkins and the like.

For practical purposes, the alloying polymer of the invention will usually contain from 10% to 20% by weight units derived from the ester but in some instances it may be desirable to include as much as 50% by weight ester units in the polymer. The alloying polymer may have any molecular weight as long as it can be dispersed in the viscose solution. Usually, the molecular weight of the alloying polymer will be within the range of from about 50,000 to 400,000. It is believed that the units derived from acrylic or methacrylic acid in the copolymer chain are the ones which are primarily responsible for the improved absorbency of the fibers. It should be noted, however, that the fibers of the invention are more absorbent than the prior art fibers containing the homopolymer of acrylic acid.

Although the alloying polymer of the invention mixed with the viscose solution may be neutralized or partially neutralized with any suitable alkali metal hydroxide or ammonium, sodium hydroxide is preferred. The alloying polymer is preferably neutralized to a pH of from about 1 to 7 before spinning of the viscose solution containing it.

Any suitable purification process may be used to convert the spun fiber into a fiber suitable for use in an absorbent article such as for example the procedure of Table II.

TABLE II

| Step | Solutions and Sequence | Conc.% | Temp. °C | Pressure Lbs. | Time Mins. |
|---|---|---|---|---|---|
| 1 | Sulfuric Acid | 0.10-0.15 | 25-35 | 9-10 | 40 |
| 2 | Soft Water (after 5 min., clean filter) | 5 ppm Max. H. | 25-35 | 9-10 | 120 |
| 3 | Desulfuring Sodium Sulfide | Na₂S:0.45-0.55 NaOH:0.05-0.10 | 50-55 | 9-10 | 40 |
| 4 | Soft Water (after 5 min., clean filter) | 5 ppm Max. H. | 25-35 | 9-10 | 80 |
| 5 | Acetic Acid | 0.01 | 25-35 | 9-10 | 40 |
| 6 | NOPCO 1921-D | 0.2 | 35-45 | 9-10 | 40 |

Although the invention has been described in detail for the purpose of illustration, it is to be understood that such detail is solely for that purpose and that variations can be made therein by those skilled in the art without departing from the spirit and scope of the invention except as it may be limited by the claims.

I claim:

1. A fluid absorbent cellulose fiber containing in an admixture with cellulose an alkali metal salt or ammonium salt of a polymer having repeating units derived from an aliphatic ester of acrylic acid or methacrylic acid and having repeating units derived from at least one member from the group consisting essentially of acrylic acid, methacrylic acid or an anhydride thereof and acrylamidoalkyl sulfonic acid.

2. The fluid absorbent regenerated cellulose fiber of claim 1 wherein the said salt is a member selected from the group consisting of a salt of
   (a) a copolymer of acrylic acid or methacrylic acid and an aliphatic ester of acrylic acid or methacrylic acid,
   (b) a terpolymer of acrylic acid, methacrylic acid and an aliphatic ester of acrylic acid or methacrylic acid,
   (c) a polymer of (a) or (b) also containing units derived from an unsaturated aliphatic dicarboxylic acid,
   (d) a polymer of (a), (b), or (c) also containing units derived from an acryloamidoalkyl sulfonic acid or an unsaturated phosphorous acid; and
   (e) a polymer of an acryloamidoalkyl sulfonic acid and an aliphatic ester of acrylic acid or methacrylic acid;
   said fiber being more absorbent than fibers of the same regenerated cellulose fibers free from an alloying polymer.

3. The fiber of claim 1 containing an alkali metal salt or ammonium salt of a copolymer of acrylic acid or methacrylic acid and an alkyl ester of acrylic acid or methacrylic acid.

4. The fiber of claim 1 containing an alkali metal salt or ammonium salt of a terpolymer containing units derived from acrylic acid, methacrylic acid, and an aliphatic ester of acrylic acid or an aliphatic ester of methacrylic acid.

5. The fiber of claim 2 containing an alkali metal salt or ammonium salt of a copolymer of (a) or (b) containing an unsaturated aliphatic dicarboxylic acid.

6. The fiber of claim 2 containing an alkali metal salt or ammonium salt of a polymer of (a), (b) or (c) containing an acryloamidoalkyl sulfonic acid or an unsaturated phosphorous acid.

7. The fiber of claim 3 wherein the copolymer is acrylic acid and an ester of acrylic acid or methacrylic acid.

8. An article of manufacture for absorbing fluids comprising regenerated cellulose fibers containing in physical mixture with said cellulose an alkali metal salt or ammonium salt of a polymer having repeating units derived from an aliphatic ester of acrylic acid or methacrylic acid and having repeating units derived from at least one member of the group consisting essentially of acrylic acid, methacrylic acid or an anhydride thereof and acrylamidoalkyl sulfonic acid.

9. The article of manufacture of claim 8 comprising a fluid absorbent mass of fibers comprising regenerated cellulose and an alkali metal or ammonium salt of
   (a) a copolymer of acrylic acid or methacrylic acid and an aliphatic ester of acrylic acid or methacrylic acid, $$Q = \frac{\text{Swollen weight} - \text{dry weight}}{\text{dry weight}} \times 100$$

U.S. Pat. No. 3,670,069, column 6, describes a method for making this determination. The secondary swelling is an indication of the fluid absorbency of the fiber, the larger the percentage, the greater the absorbency of the fiber.

The saline retention value (SRV) is determined by the same procedure as the water retention value except that a 1% aqueous solution of sodium chloride is substituted for water.

In the following examples, all parts and percentages are by weight unless otherwise specified.

EXAMPLE I

In this Example a rayon fiber which does not contain any alloying polymer or copolymer was prepared for comparison with fibers of the invention.

A ripened viscose solution containing 8.4% cellulose, 4.8% sodium hydroxide, and 2.3% sulfur was extruded through a spinneret having 480 holes to produce filaments of 1100 denier. The spinbath contained 5.5% sulfuric acid, 24% sodium sulfate, and 0.95% zinc sulfate in water. The temperature of the spinbath was 50° C. After passing through the spinbath, the resulting fibers were further processed, stretched 37% and cut into staple fibers. The pH of the fiber was adjusted with sodium bicarbonate to provide an alkaline fiber which was treated with a 0.3% aqueous solution of Tween 20 to surface finish the fiber.

After conditioning, water retention (WRV), as secondary swelling, and saline retention in 1% sodium chloride, (SRV), determinations were made on the staple fiber. The water retention (WRV) of the sample was 71% and the saline retention (SRV) was 67%.

EXAMPLE II

Example I was repeated except that 10% by weight of an acrylic acid polymer as a 19% aqueous solution having a Brookfield viscosity of 9900 cps determined with a No. 2 spindle at 3 RPM was mixed with the viscose solution by injection just prior to extrusion. The water retention value (WRV) and saline retention value (SRV) were determined and the results are recorded in Table I.

EXAMPLE III

A copolymer containing 90% acrylic acid and 10% n-butyl acrylate was prepared by mixing 112.5 parts acrylic acid and 12.5 parts of n-butylacrylate in 875 parts of distilled water. About 24 parts isopropanol were added as a chain transfer agent to control the molecular weight of the resulting copolymer. The solution was heated to 65° C. and 0.4 parts potassium persulfate was added. After 1½ hours of heating at 65° C., the polymerization was complete and 100 parts of a 50% aqueous solution of sodium hydroxide was added to raise the pH to about 6.5. The polymer solution had a Brookfied viscosity of 2875 cps (#2 spindle, 6 RPM at room temperature of about 20° C.)

Sufficient of the resulting aqueous solution of copolymer was mixed with a second portion of the viscose solution used in Example I to provide the equivalent of 10% by weight acrylic acid. A staple fiber was then prepared by the procedure used in Example I and the water retention value (WRV) and saline retention value (SRV) were determined and are recorded in Table I.

EXAMPLE IV

A copolymer containing 80% acrylic acid and 20% ethyl acrylate was prepared by mixing 200 parts acrylic acid and 50 parts of ethyl acrylate in 75 parts of distilled water. About 63 parts isopropanol were added as a chain transfer agent to control the molecular weight of the resulting copolymer. The solution was heated to 65° C. and 0.4 part potassium persulfate was added. After 1½ hours of heating at 65° C., the polymerization was complete and 180 parts of a 50% aqueous solution of sodium hydroxide were added. The polymer solution had a Brookfield viscosity of 31000 cps (#3 spindle, 3 RPM at room temperature of about 20° C.) at a solids content of 26%.

The copolymer solution was diluted to 20% and was mixed with a portion of the viscose solution used in Example I to provide the equivalent of 10% by weight acrylic acid. A staple fiber was then prepared by the procedure used in Example I and the water retention value (WRV) and saline retention value (SRV) were determined and are recorded in Table I.

EXAMPLE V

A copolymer containing 90% acrylic acid and 10% lauryl methacrylate was prepared by mixing 225 parts acrylic acid and 25 parts of lauryl methacrylate in 750 parts of distilled water. About 95 parts isopropanol were added as a chain transfer agent to control the molecular weight of the resulting copolymer. The solution was heated to 65° C. and 0.4 parts potassium persulfate was added. After 1½ hours of heating at 65° C., the polymerization was complete and 150 parts of a 50% aqueous solution of sodium hydroxide were added. The polymer solution had a Brookfied viscosity of 7560 cps (#2 spindle, 3 RPM at room temperature of about 20° C.)

Sufficient of the resulting aqueous solution containing 26% by weight copolymer was mixed with a portion of the viscose solution used in Example I to provide the equivalent of 10% by weight acrylic acid. A staple fiber was then prepared by the procedure used in Example I and the water retention (WRV) and saline retention (SRV) were determined and are recorded in Table I.

EXAMPLE VI

The sodium salt of 2-acrylamido-2-methylpropane sulfonic acid (AMPS) was prepared by adding 225 parts of AMPS to a cold (10° C.) solution of 43.5 parts sodium hydroxide in 450 parts water. To the solution of sodium AMPS was added 25 parts n-butyl acrylate (nBA), 50 parts isopropanol, and 200 parts water. The solution was heated to 65° C. while purging with nitrogen. Potassium persulfate, 0.5 parts, was added to the mixture and the temperature maintained at 65° C. for 1½ hours. The resultant polymer solution had a Brookfield viscosity of 3000 cps (#2 spindle, 6 RPM at room temperature of about 20° C.)

Sufficient of the resulting aqueous copolymer was mixed with viscose as in Example I to give an equivalent of 10% by weight of AMPS. A staple fiber was then prepared by the procedure used in Example I and the water retention value (WRV) and saline retention value (SRV) were determined. The results are listed in Table I.

(b) a terpolymer of acrylic acid, methacrylic acid and an aliphatic ester of acrylic acid or methacrylic acid, (c) a polymer of (a) or (b) also containing units derived from an unsaturated aliphatic dicarboxylic acid, (d) a polymer of (a), (b) or (c) also containing units derived from an acryloamidoalkyl sulfonic acid or an unsaturated phosphorous acid, or (e) a polymer of an acryloamidoalkyl sulfonic acid and an aliphatic ester of acrylic acid or methacrylic acid;

said fibers being more absorbent than fibers of the same regenerated cellulose free from an alloying polymer.

10. The article of claim 8 wherein the regenerated cellulose contains an alkali metal salt or an ammonium salt of a terpolymer of acrylic acid, methacrylic acid and an aliphatic ester of acrylic acid or methacrylic acid.

11. The article of claim 9 wherein the fiber contains (a).

12. A method of improving the fluid absorbency of a regenerated cellulose fiber which comprises physically admixing in the fiber an alkali metal salt or ammonium salt of (a) a copolymer of acrylic acid or methacrylic acid and an aliphatic ester of acrylic acid or methacrylic acid, (b) a terpolymer of acrylic acid, methacrylic acid and an aliphatic ester of acrylic acid or methacrylic acid, (c) a copolymer of (a) or (b) also containing units derived from an unsaturated aliphatic dicarboxylic acid, (d) a copolymer of (a), (b) or (c) also containing units derived from an acryloamidoalkyl sulfonic acid or unsaturated phosphorous acid, or (e) a polymer of an acryloamidoalkyl sulfonic acid and an aliphatic ester of acrylic acid or methacrylic acid;

said fiber being more absorbent than non-alloyed regenerated cellulose fibers.

13. The method of claim 12 wherein a copolymer of acrylic acid or methacrylic acid and an alkyl ester of acrylic acid or methacrylic acid is physically admixed in the fiber.

14. A method of improving the fluid absorbency of a regenerated cellulose fiber which comprises physically admixing in the fiber an alkali metal salt or ammonium salt of a polymer of acrylic acid or methyacrylic acid or anhydride thereof and an aliphatic ester of acrylic acid or methacrylic acid.

15. A method of making a fluid absorbent fiber comprising mixing an alkali metal salt or ammonium salt of (a) a copolymer of acrylic acid or methacrylic acid and an aliphatic ester of acrylic acid or methacrylic acid, (b) a terpolymer of acrylic acid, methacrylic acid and an aliphatic ester of acrylic acid or methacrylic acid, (c) a polymer of (a) or (b) also containing units derived from an unsaturated aliphatic dicarboxylic acid, (d) a polymer of (a), (b) or (c) also containing units derived from an acryloamidoalkyl sulfonic acid or unsaturated phosphorous acid, or (e) a polymer of an acryloamidoalkyl sulfonic acid and an aliphatic ester of acrylic acid or methacrylic acid;

with a viscose solution, extruding the mixture, regenerating the cellulose, and purifying and drying the resulting fiber.

* * * * *